(12) United States Patent
Berenshteyn

(10) Patent No.: US 10,500,338 B2
(45) Date of Patent: Dec. 10, 2019

(54) PREFILLED DISPOSABLE INJECTION DEVICE

(71) Applicant: Merck Sharp & Dohme Corp., Rahway, NJ (US)

(72) Inventor: Annaniy Berenshteyn, Edgewater, NJ (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 25 days.

(21) Appl. No.: 15/561,145

(22) PCT Filed: Apr. 12, 2016

(86) PCT No.: PCT/US2016/027019
§ 371 (c)(1),
(2) Date: Sep. 25, 2017

(87) PCT Pub. No.: WO2016/168137
PCT Pub. Date: Oct. 20, 2016

(65) Prior Publication Data
US 2018/0104418 A1    Apr. 19, 2018

Related U.S. Application Data

(60) Provisional application No. 62/148,972, filed on Apr. 17, 2015.

(51) Int. Cl.
*A61M 5/24* (2006.01)
*A61M 5/315* (2006.01)
*A61J 1/06* (2006.01)

(52) U.S. Cl.
CPC ............ *A61M 5/2425* (2013.01); *A61M 5/24* (2013.01); *A61M 5/2455* (2013.01);
(Continued)

(58) Field of Classification Search
CPC .............. A61M 5/2425; A61M 5/2455; A61M 2005/2407; A61M 5/31511; A61M 5/24;
(Continued)

(56) References Cited

U.S. PATENT DOCUMENTS 8,262,604 B2    9/2012 Asmussen et al.
2005/0124940 A1    6/2005 Martin et al.
(Continued)

FOREIGN PATENT DOCUMENTS

EP    2623143 A1    8/2013

OTHER PUBLICATIONS

Cocoman, A. et al., Intramuscular injections: a review of best practice for mental health nurses, Journal of Psychiatric and Mental Health Nursing, 2008, p. 424-434, vol. 15.

*Primary Examiner* — Bhisma Mehta
*Assistant Examiner* — Hamza A Darb
(74) *Attorney, Agent, or Firm* — Janet E. Fair; Catherine D. Fitch

(57) ABSTRACT

A drug delivery device comprising a drug container extending between a distal end and a proximal end and is capable of being compressed into a single plane; a body extending between proximal and distal ends comprising a hollow space for containing the drug container; and a plunger extending between proximal and distal ends, wherein the distal end of the plunger engages telescopically with the proximal end of the body, wherein the plunger comprises at least one pair of protrusions, wherein the protrusion is capable of compressing the drug container as the plunger moves towards the proximal end of the drug delivery device, by applying a force to the drug container that is perpendicular to the movement of the plunger.

15 Claims, 17 Drawing Sheets

(52) U.S. Cl.
CPC ............ *A61M 5/31511* (2013.01); *A61J 1/06* (2013.01); *A61M 2005/2407* (2013.01)

(58) Field of Classification Search
CPC ......... A61M 2005/31516; A61M 2005/31518; A61J 1/06
See application file for complete search history.

(56) References Cited

U.S. PATENT DOCUMENTS

| | | |
|---|---|---|
| 2006/0069350 A1 | 3/2006 | Buenger et al. |
| 2007/0051362 A1 | 3/2007 | Sullivan et al. |
| 2008/0195056 A1 | 8/2008 | Bishop et al. |
| 2010/0036318 A1 | 2/2010 | Raday et al. |
| 2011/0270220 A1* | 11/2011 | Genosar ................ A61J 1/067 604/506 |
| 2014/0171872 A1* | 6/2014 | Mathews .............. A61M 5/002 604/136 |
| 2017/0007766 A1* | 1/2017 | Basile ................ A61M 5/2425 |

* cited by examiner

PREFILLED DISPOSABLE INJECTION DEVICE

CROSS-REFERENCE TO RELATED APPLICATIONS

This application is a U.S. National Phase application under 35 U.S.C. § 371 of PCT Application No. PCT/US2016/027019, filed Apr. 12, 2016, which published as WO2016/168137 A1 on Oct. 20, 2016, and claims priority under 35 U.S.C. § 365(b) from U.S. provisional patent application No. 62/148,972, filed Apr. 17, 2015.

FIELD OF THE INVENTION

The present invention relates generally to drug delivery devices. Specifically, the invention is directed to an uncomplicated, low-cost, prefilled injection device for intramuscular injection.

BACKGROUND

Intramuscular injections are used to administer medication that requires a relatively quick uptake by the body with a reasonably prolonged action. With an intramuscular injection, the skin is punctured with a needle and the medication is administered deep into a large muscle of the body.

Intramuscular injections are either administered by a medical professional or are self-administered and can be administered using a pre-filled injection device or, first drawing the medication up through a needle into an injection device from a separate vial and then administering the medication. As far as ease of use, it is preferable to use a pre-filled injection device since there is no need to draw up medication from a separate vial into the injection device. Moreover, in some cases when medication needs to be drawn up into the injection device from a separate vial, the needle of the injection device needs to be changed after the medication has been drawn up into the injection device. Many protocols recommend using a filtered needle or a small needle to draw up medication from a vial to an injection device in order to reduce any likelihood that glass or other debris will be injected into the patient and then, preferably, changing the needle, switching to a larger needle appropriately sized for the size of the patient and the specific injection site. Both of these draw backs, transferring medication from a separate vial to an injection device and changing needles are avoided when a pre-filled injection device is used (Cocoman A. & Murray J. (2008) Journal of Psychiatric and Mental Health Nursing 15, 424-434).

However, most pre-filled injection devices, specifically automatic ones are complex and expensive to manufacture and in some cases, are not capable of delivering medication at a slow, steady rate, preferably not to exceed 1 mL per 10 seconds. A slow, steady rate promotes comfort and allows time for the tissues to expand and begin absorbing the solution. Examples of injection devices are described in EP2623143, US20050124940, U.S. Pat. No. 8,262,604 and US20080195056.

SUMMARY

The injection device described herein overcomes many of the above-described drawbacks. The injection device described herein is directed to an uncomplicated, low-cost, prefilled injection device for intramuscular injection.

The drug delivery device described herein includes a prefilled drug container, a body, a plunger and a needle.

The body of the drug delivery device described herein houses the drug container. The plunger is capable of moving telescopically within the body and comprises at least one pair of protrusions, wherein the protrusions work in concert to compress the drug container by applying a force to the drug container that is perpendicular to the movement of the plunger, as the plunger moves towards the distal end of the body. The drug container of the drug delivery device described herein is capable of being compressed into a single plane.

For the purpose of clarity, orientation references are hereby established for the description of this invention. The term "proximal" refers to a position that is close to the body of the person injecting a drug into the patient with the device. The term "distal" refers to a position that is away from the body of the person injecting the drug into the patient with the device.

Described herein is a drug delivery device comprising a drug container extending between a distal end and a proximal end comprising an outlet port located at the distal end of the drug container and capable of being compressed into a single plane; a body extending between proximal and distal ends comprising a hollow space for containing the drug container; and a plunger extending between proximal and distal ends, wherein the distal end of the plunger engages telescopically with the proximal end of the body, wherein the plunger comprises at least one pair of protrusions, wherein the protrusions work in concert to compress the drug container as the plunger moves towards the distal end of the body, by applying a force to the drug container that is perpendicular to the movement of the plunger.

In certain embodiments of the drug delivery device described herein, the drug container contains a drug.

In certain embodiments of the drug delivery device described herein, the drug container comprises a tapered distal portion located at the distal end of the drug container; a tapered proximal portion located at the proximal end of the drug container; and a central portion having a constant cross section located between the distal portion and the proximal portion of the drug container. In certain embodiments, the central portion of the drug container has a hexagonal prism shape.

In certain embodiments of the drug delivery device described herein, the plunger comprises two pairs of protrusions.

In certain embodiments of the drug delivery device described herein, the body comprises at least one flange located at the proximal end of the body. In certain embodiments the body comprises a pair of flanges located at the proximal end of the body.

In certain embodiments of the drug delivery device described herein, the body comprises an outlet port that is capable of fitting telescopically over the outlet port of the drug container.

In certain embodiments of the drug delivery device described herein, the drug delivery device further comprises a needle that attaches to the outlet port of the body and is in communication with the outlet port of the drug container.

In certain embodiments of the drug delivery device described herein, the body comprises at least one pair of notches located proximal to the proximal end of the body.

In certain embodiments of the drug delivery device described herein, the body comprises a pair of notches located proximal to the distal end of the body.

In certain embodiments of the drug delivery device described herein, the plunger comprises one pair of lift springs that can engage the pair of notches on the body to secure the drug delivery device in a locked position.

In certain embodiments of the drug delivery device described herein, the body comprises at least one internal guide rail.

In certain embodiments of the drug delivery device described herein, the plunger comprises a slot to engage the guide rail of the body.

Also described herein are methods of manufacturing the drug containers of the drug delivery devices described herein, wherein the drug container is made using blow-fill-seal technology.

BRIEF DESCRIPTION OF THE FIGURES

The foregoing and other features and advantages of the invention will be apparent from the following, more particular description of a preferred embodiment of the invention, as illustrated in the accompanying drawings wherein like reference numbers generally indicate identical, functionally similar, and/or structurally similar elements.

DESCRIPTION

Figure 1:
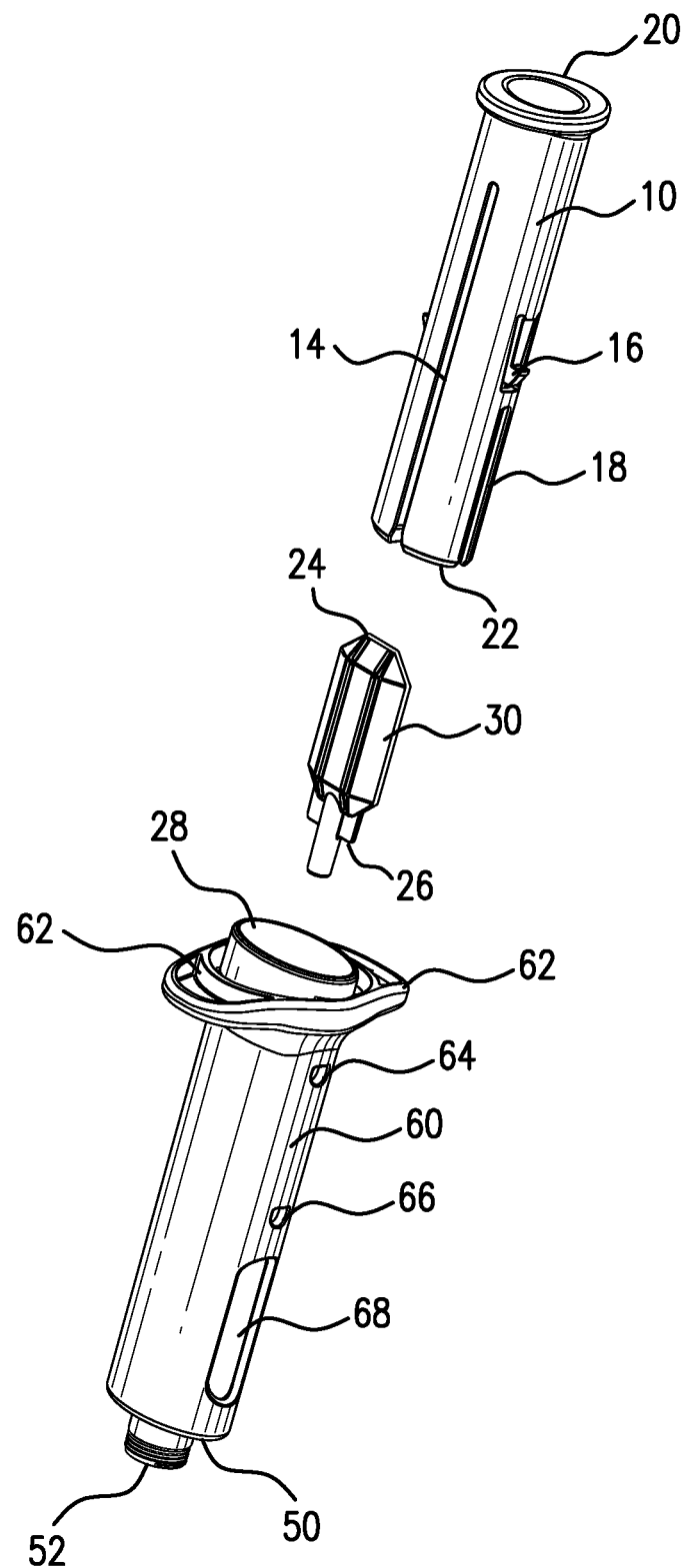
FIG. 1 is an exploded view of an embodiment of the drug delivery device described herein.

Referring to the figures, wherein like reference numerals designate like elements throughout the drawings, FIG. 1 is an exploded view of an embodiment of a drug delivery device described herein. FIG. 1 shows an embodiment of a plunger 10, a drug container 30 and a body 60. Plunger 10 has a proximal end 20 and a distal end 22. The plunger shown in FIG. 1 shows a pair of lift springs 16. Lift springs 16 are capable of engaging notches 64 and 66 located on the body 60. Plunger 10 also has a slot 14. Slot 14 is capable of engaging an internal guide rail (not shown) located on the body 60. Plunger 10 also includes space 18. Space 18 is useful for allowing the drug container 30 to collapse into and expand along a single flat plane.

FIG. 1 also shows drug container 30. Drug container 30 has a proximal end 24 and a distal end 26.

FIG. 1 also shows an embodiment of a body 60 of the drug delivery device described herein. Body 60 has a proximal end 28 and a distal end 50. Body 60 also has a pair of finger flanges 62. Body 60 also includes two pairs of notches, proximal notches 64 located proximal to the proximal end of the body 60 and distal notches 66 located proximal to the distal end of body 60. Body 60 also includes a window 68 to view the drug container 30, once the drug container is housed in the body. Body 60 also has an outlet port 52. Outlet port 52 is capable of engaging a needle. In the embodiment shown in FIG. 1, the engagement of a needle to outlet port 52 is a threaded engagement. However, in certain embodiments, the mechanical engagement of the needle to the body comprises any of, a Luer Lock, Luer taper, tapered connection, helical threads, a bayonet fitting connection, or an integral latch feature. In certain embodiments, the needle is attached to the drug delivery device prior to use.

Figure 2:
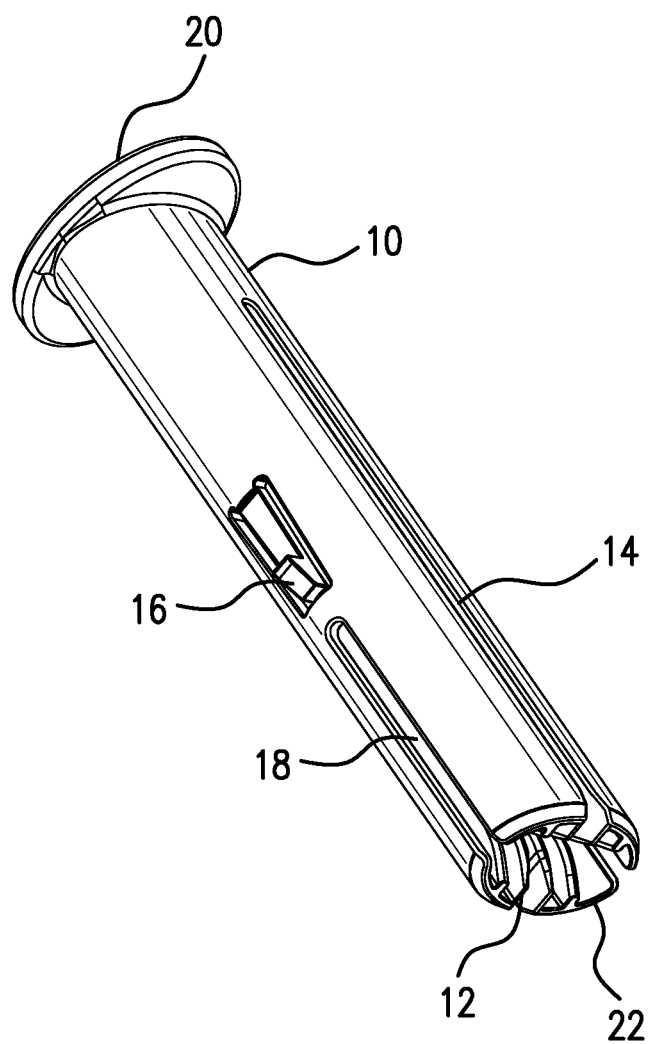
FIG. 2 is a perspective view of a plunger of an embodiment of the drug delivery device described herein.

FIG. 2 is a perspective view of a plunger of an embodiment of the drug delivery device described herein. As shown in FIG. 2, plunger 10 has a proximal end 20 and a distal end 22. The plunger shown in FIG. 2 shows one of a pair of lift springs. Lift springs 16 are capable of engaging notches located on the body. The purpose of the engagement of the lift springs on the plunger and the notches on the body is to secure the drug delivery device in an initial or pre-injection position and then to secure the drug delivery device in a second or post-injection position. Thus, in alternative embodiments, other mechanisms can be used to achieve the same function, such as mating serrated teeth formed on both the outside surface of the plunger and the inside surface of the body.

Plunger 10 also has a slot 14. Slot 14 is capable of engaging an internal guide rail located on the body of the drug delivery device described herein. Plunger 10 also includes space 18. Space 18 is useful for allowing the drug container 30 to collapse into and expand along a single flat plane.

Also shown in FIG. 2 at the distal end of the plunger are a series of protrusions 12. As shown in FIG. 2, protrusions 12 are organized into cross-facing pairs. As the plunger moves downward toward the proximal end of the body, the protrusions 12 work in concert to compress the drug container, by applying a force to the drug container that is perpendicular to the movement of the plunger.

Figure 3:
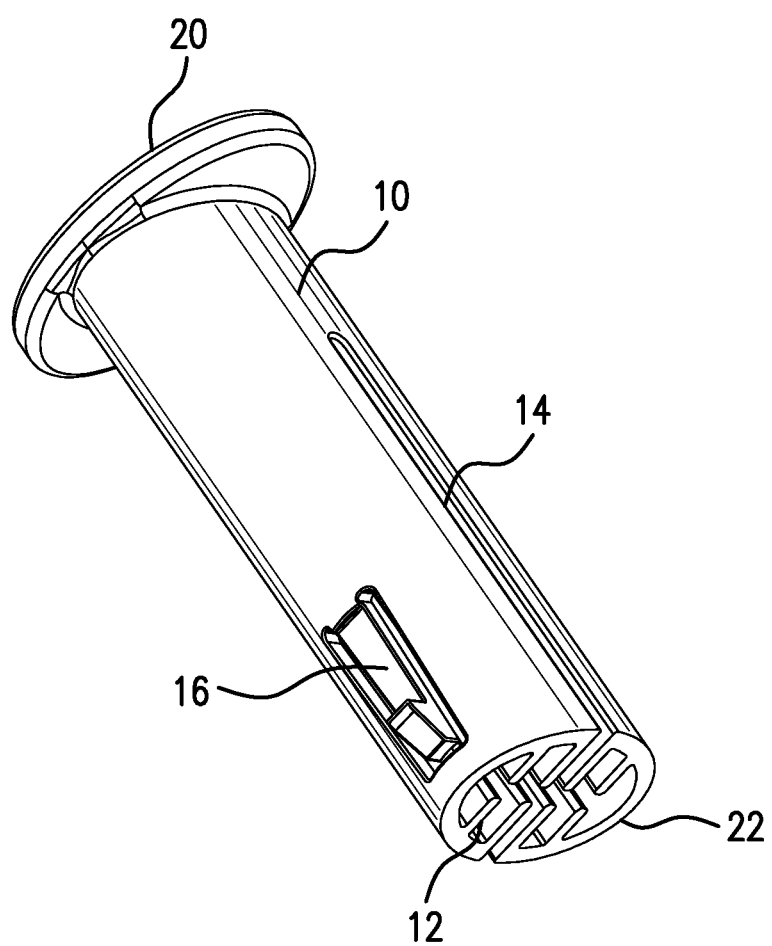
FIG. 3 is a perspective view of a plunger of an embodiment of the drug delivery device described herein.

FIG. 3 is a perspective view of a plunger of an embodiment of the drug delivery device described herein. As shown in FIG. 3, plunger 10 has a proximal end 20 and a distal end 22. The plunger shown in FIG. 3 shows one of a pair of lift springs 16. Plunger 10 also has a slot 14.

In the embodiment of the plunger shown in FIG. 3, the plunger 10 has no space 18 as shown in FIG. 2.

Also shown in FIG. 3 at the distal end 22 of the plunger 10 are eight protrusions 12. As shown in FIG. 3, the eight protrusions are organized into cross-facing pairs where each member of a protrusion pair faces the other member of the protrusion pair. The protrusions 12 work in concert to compress the drug container as the plunger moves towards the distal end of the body, by applying a force to the drug container that is perpendicular to the movement of the plunger.

Figure 4:
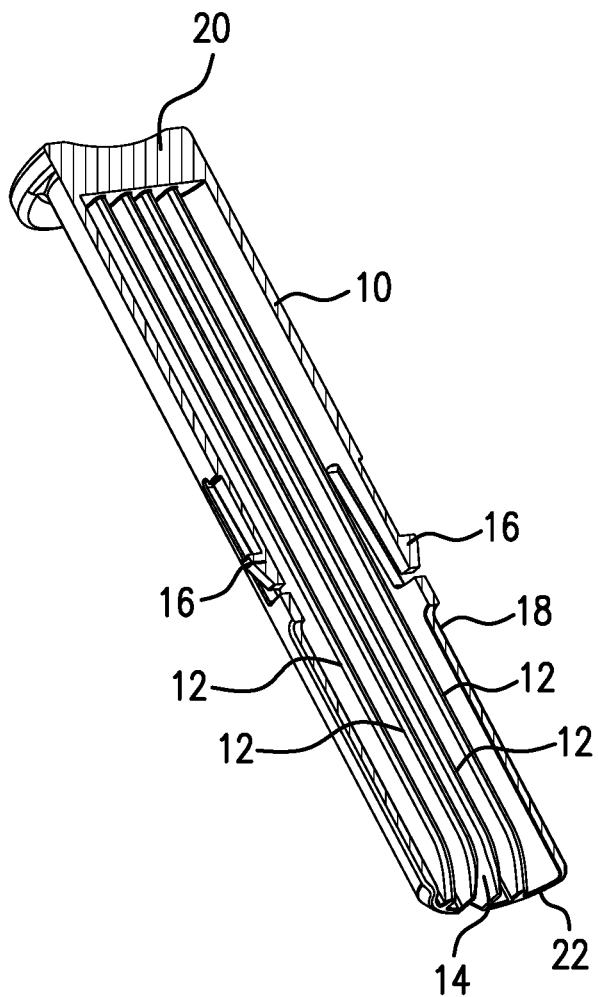
FIG. 4 is a cross-sectional view of a plunger of an embodiment of the drug delivery device described herein.

FIG. 4 is a cross-sectional view of an embodiment of a plunger of the drug delivery device described herein. As shown in FIG. 4, plunger 10 has a proximal end 20 and a distal end 22. The plunger shown in FIG. 4 shows a pair of lift springs 16. Plunger 10 also has a slot 14. Plunger 10 also includes space 18. Space 18 is useful for allowing the drug container 30 to collapse into and expand along a single flat plane.

Also shown in FIG. 4, are four protrusions 12. Each protrusion 12 is one of a protrusion pair. The protrusion pairs work in concert to compress the drug container as the plunger 10 moves towards the distal end of the body, by applying a force to the drug container that is perpendicular to the movement of the plunger. In the embodiment shown in FIG. 4, each protrusion 12 tapers near the distal end 22 of the plunger 10. The protrusion taper allows for gradual engagement with the drug container, thus requiring less force to compress the drug container. In alternative embodiments, the protrusions are not tapered. In still other embodiments the distal end of the protrusions comprises a rounded edge or other means to allow for gradual engagement of the drug container with the protrusions.

Figure 5:
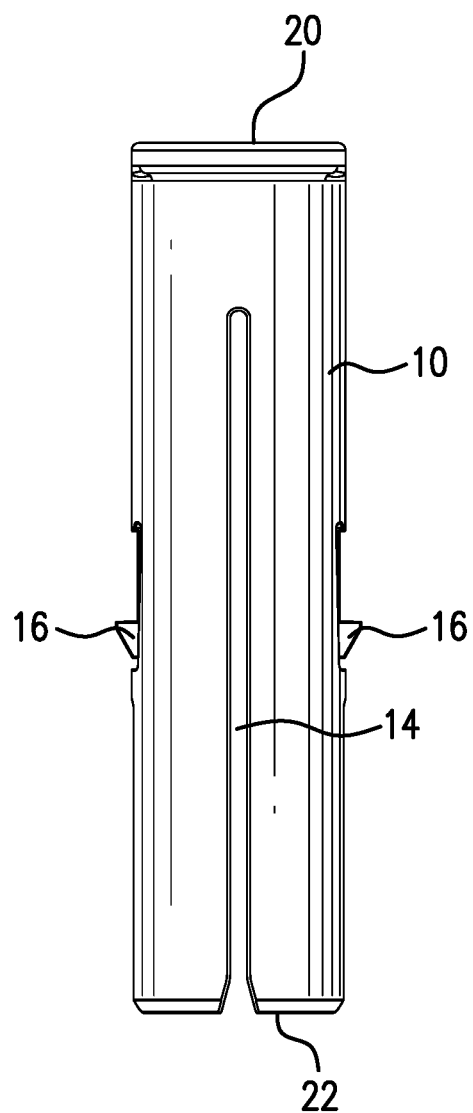
FIG. 5 is a perspective view of a plunger of an embodiment of the drug delivery device described herein.

FIG. 5 is a perspective view of an embodiment of plunger of the drug delivery device described herein. As shown in FIG. 5, plunger 10 has a proximal end 20 and a distal end 22. The plunger shown in FIG. 5 shows a pair of lift springs 16. Lift springs 16 are capable of engaging notches on the body of the drug delivery device described herein. Plunger 10 also has a slot 14. Slot 14 is capable of engaging an internal guide rail located on the body of the drug delivery device described herein.

Figure 6:
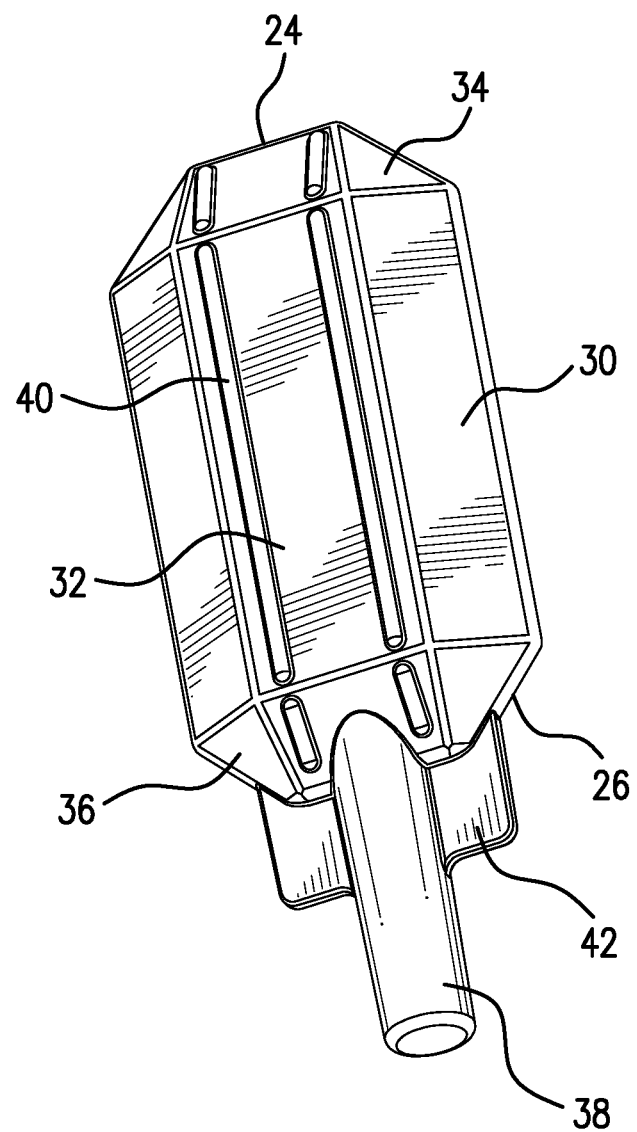
FIG. 6 is a perspective view of a drug container of an embodiment of the drug delivery device described herein.

FIG. 6 is a perspective view of an embodiment of a drug container of the drug delivery device described herein. Suitable drug containers for the drug delivery device described herein can have any three dimensional shape that is capable of being compressed by the protrusions into a relatively flat plane. As shown in FIG. 6, drug container 30 has distal end 26 and a proximal end 24. Drug container 30 has a tapered distal portion 36 located at the distal end 26 of the drug container 30 and a tapered proximal portion 34 located at the proximal end 24 of the drug container 30. Drug container 30 also has a central portion 32 located between the distal portion 36 and the proximal portion 34 of the drug container 30. The central portion 32 of drug container 30 has a constant cross section.

Also as shown in FIG. 6, drug container 30 has ribs 40 that run from the proximal end 24 of the drug container to the distal end 26 of the drug container. Ribs function to provide support to the drug container and are optional. In certain embodiments, the drug container has no ribs. In other embodiments, the ribs can be oriented in a different way. Ribs can run diagonally across the drug container. Ribs can be located in a specific section such as the proximal portion, distal portion or central portion. In certain embodiments, the ribs can run latitudinally around the drug container. In certain embodiments, drug container 30 also has orientation wings 42 located at the distal end 26 of the drug container. Orientation wings 42 can assist in properly orienting the drug container in the body of the drug delivery device described herein and are also optional. In certain embodiments, the drug container does not have wings. In still other embodiments, the drug container can have wings or tabs at other locations on the drug container to aid in orienting the drug container in the body of the drug delivery device described herein. Also shown in FIG. 6 is outlet port 38 on drug container 30. Outlet port 38 communicates with an outlet port on the body to provide a means for the drug contained in the drug container to exit the drug delivery device and be delivered to the patient.

Figure 7:
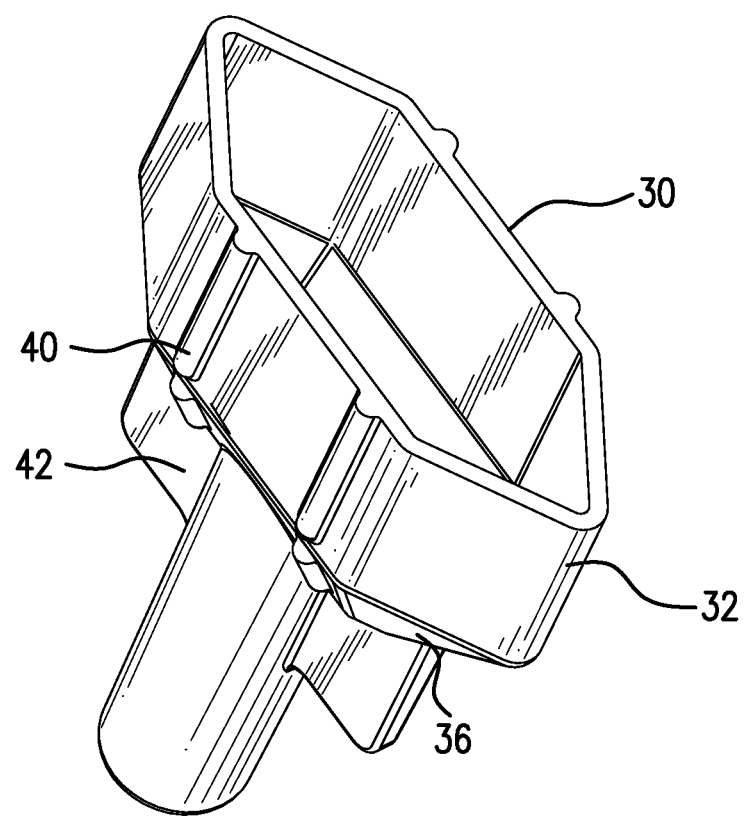
FIG. 7 is a cross-sectional view of an embodiment of the drug container described herein.

FIG. 7 is a cross-sectional view of an embodiment of a drug container of the drug delivery device described herein. As shown in FIG. 7, drug container 30 has a central portion 32 located between the distal portion 36 and the proximal portion (not shown) of the drug container 30. In the embodiment shown in FIG. 7, the central portion 32 of drug container 30 has a constant cross section and in the embodiment shown in FIG. 7, the central portion 32 of the drug container has a hexagonal prism shape. As discussed above, the drug container can be any three dimensional shape that is capable of collapsing into a relatively single plane. In certain embodiments, the drug container can have a cylindrical, spheroidal or other three dimensional prismatic shape. Also shown on the drug container 30 in FIG. 7, are optional features ribs 40 and orientation wings 42. Also shown in FIG. 7 is outlet port 38 on drug container 30.

Figure 8:
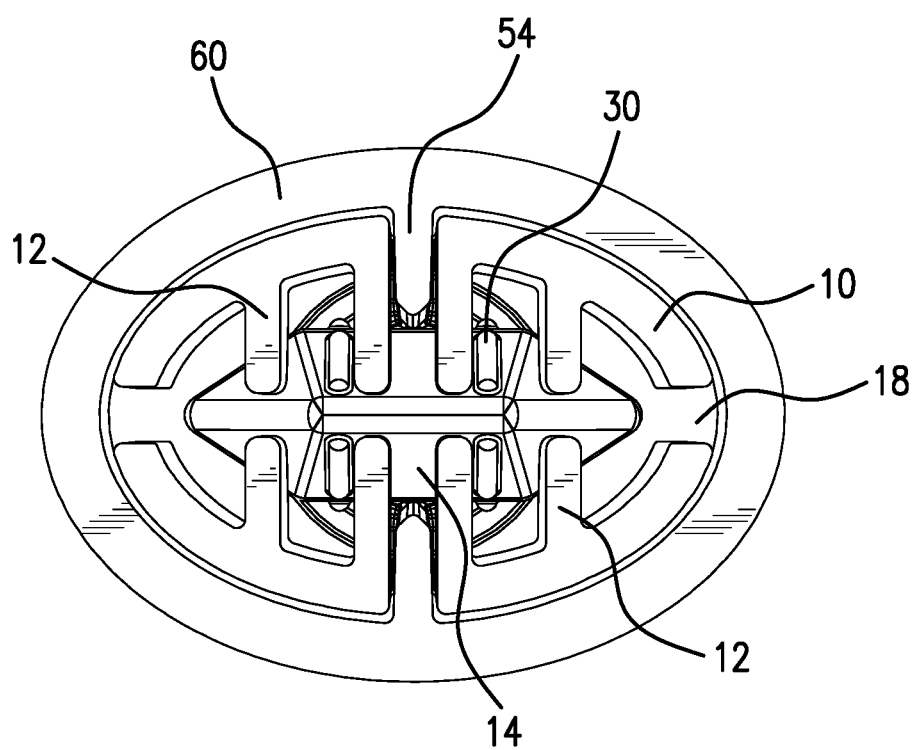
FIG. 8 is a top view of a plunger, drug container and body of an embodiment of the drug delivery device described herein.

FIG. 8 is a top view of the body, plunger and drug container. As shown in FIG. 8, plunger 10 has four pairs of protrusions 12. The protrusions work in concert to compress the drug container 30 as the plunger 10 moves towards the distal end of the body 60, by applying a force to the drug container 30 that is perpendicular to the movement of the plunger 10. Though the embodiment in FIG. 8 shows four pairs of protrusions, in other embodiments, the plunger 10 can comprise any number of protrusions. In the embodiment shown in FIG. 8, the protrusions are aligned in cross-facing pairs. However, in other embodiments, any number of protrusions can be aligned in any manner so long as adequate force is applied to the drug container to force the drug container into a relatively flat plane. Plunger 10 forms space 18 in the drug delivery device described herein to accommodate expansion of the drug container 30 into a flat plane. Plunger 10 also includes slot 14 to accommodate guide tail 54 on the body 60.

As shown in FIG. 8, plunger 10 fits telescopically in body 60. Body 60 has guide rail 54 that engages with slot 14 on the plunger 10. As shown in FIG. 8, plunger 10 and body 60 have an oval shape, but it is contemplated that the plunger and body can be any shape so long as the changing shape of the drug container can be accommodated. In other embodiments, the shape of the plunger and body can be circular. Also shown in FIG. 8 is drug container 30. As plunger 10 is pushed into body 60, protrusions 12 apply a force to the drug container 30 that is perpendicular to the movement of the plunger 10. As protrusions 12 apply force, drug container 60 collapses into a single plane and expanding into space 18.

Figure 9:
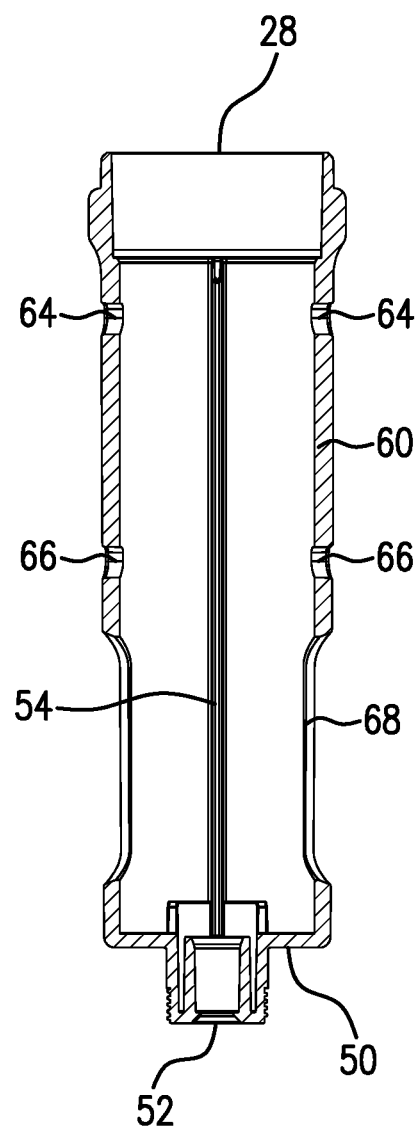
FIG. 9 is a cross-sectional view of an embodiment of a body of the drug delivery device described herein.

FIG. 9 is a cross-sectional view of an embodiment of a body of the drug delivery device described herein. Body 60 has a proximal end 28 and a distal end 50. Body 60 also includes two pairs of notches, proximal notches 64 located proximal to the proximal end 28 of the body 60 and distal notches 66 located proximal to the distal end 50 of body 60. Proximal notches 64 can engage with lift springs or other securing mechanism on the plunger to secure the drug delivery device described herein in a first or initial position, prior to administering any drug contained in the drug container. Distal notches 66 can engage with lift springs or other securing mechanism on the plunger to secure the drug delivery device described herein in a second or final position after administration of any drug contained that was initially contained in the drug container. Also, as shown in FIG. 9, body 60 incorporates a window 68 so that the drug container can be seen. Body 60 also has an outlet port 52. Outlet port 52 is capable of engaging a needle. As shown in FIG. 9, the engagement with a needle to outlet port 52 would be a threaded engagement.

As can be seen with the cross-sectional view, body 60 has a guide rail 54 located on the internal surface of body 60. Guide rail is used to engage with a slot located on the plunger to ensure that the plunger and the body are properly orientated.

Figure 10:
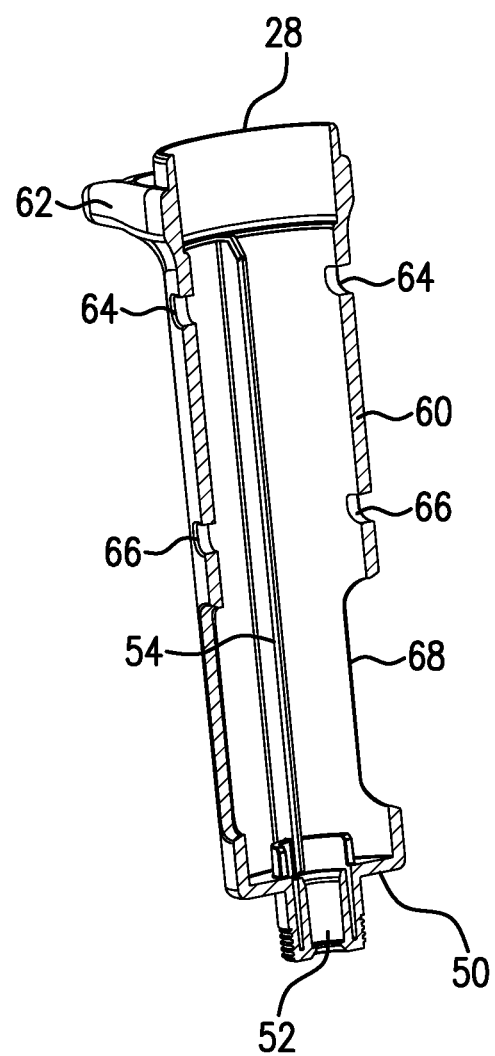
FIG. 10 is a cross-sectional view of an embodiment of a body of the drug delivery device described herein.

FIG. 10 is another cross-sectional view of an embodiment of a body of the drug delivery device described herein. FIG. 10 is similar to FIG. 9 but is slightly rotated to view finger flange 62. As shown in FIG. 10, body 60 has a proximal end 28 and a distal end 50. Body 60 also includes two pairs of notches, proximal notches 64 located proximal to the proximal end of the body 60 and distal notches 66 located proximal to the distal end of body 60. Proximal notches 64 can engage with lift springs or other securing mechanism on the plunger to secure the drug delivery device described herein in a first or initial position, prior to administering any drug contained in the drug container. Distal notches 66 can engage with lift springs or other securing mechanism on the plunger to secure the drug delivery device described herein in a second or final position after administration of any drug contained that was initially contained in the drug container. Also, as shown in FIG. 10, body 60 incorporates a window 68 so that the drug container can be seen. Body 60 also has an outlet port 52 and a guide rail 54 located on the internal surface of body 60.

Figure 11:
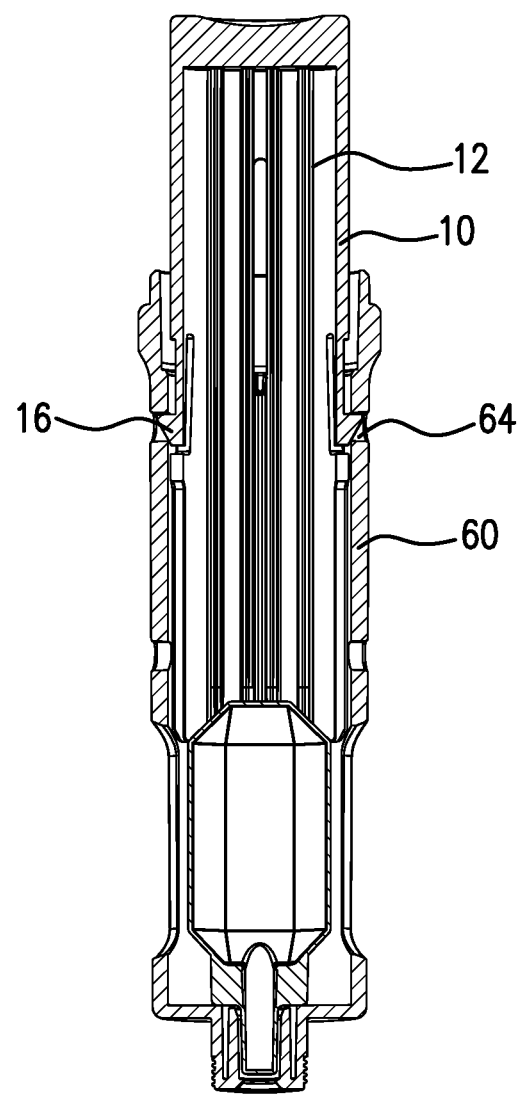
FIG. 11 is a cross-sectional view of a plunger, drug container and body of an embodiment of the drug delivery device described herein.

FIG. 11 is a cross-sectional view of one embodiment of the plunger, body and drug container of the drug delivery device described herein, wherein the plunger, body and drug container are assembled. As shown in FIG. 11, plunger 10 is telescopically engaged with body 60 and secured in an initial or first position by a pair of lift springs 16 on the plunger which are in communication with proximal notch 64 on body 60. Also shown in FIG. 11 is four protrusions 12 located on the plunger.

Figure 12:
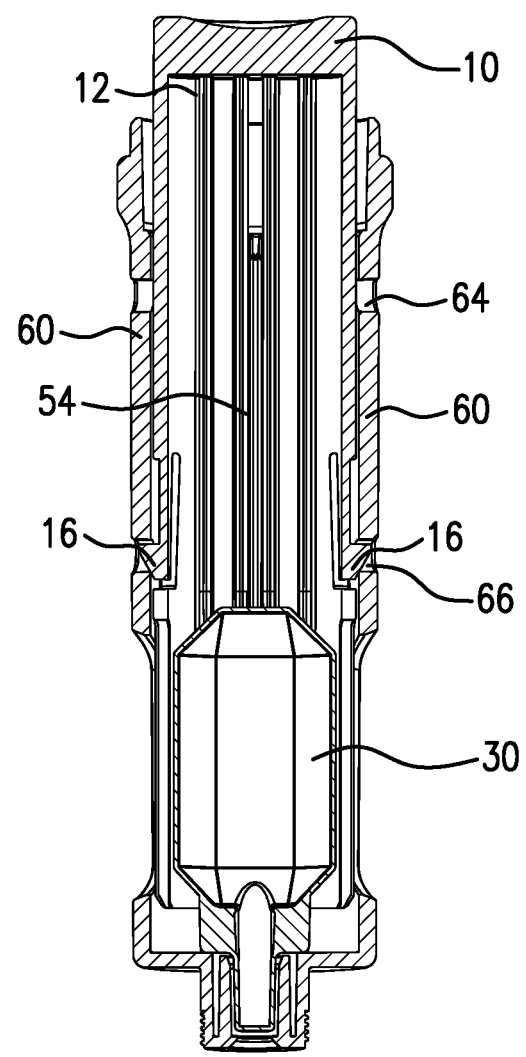
FIG. 12 is a cross-sectional view of a plunger, drug container and body of an embodiment of the drug delivery device described herein.

FIG. 12 is a cross-sectional view of one embodiment of the plunger, body and drug container of the drug delivery device described herein, wherein the plunger, body and drug container are assembled. As shown in FIG. 12, plunger 10 is telescopically engaged with body 60 and secured in a final or second position by a pair of lift springs 16 on the plunger 10, which are in communication with distal notches 66 on body 60. Also shown in FIG. 11 are four protrusions 12 located on the internal surface of the plunger 10. As plunger 10 is forced downward into body 60, lift springs 16 releases from proximal notches 64. Protrusions 12 engage drug container 30 applying a force to the drug container 30 that is perpendicular to the movement of the plunger 10. This force compresses the drug container in a single plane. The movement of the plunger 10 is stopped when lift springs 16 engage with distal notches 66.

As can be seen with the cross-sectional view, body 60 has a guide rail 54 located on the internal surface of body 60. Guide rail is used to engage with a slot located on the plunger to ensure that the plunger and the body are properly orientated.

Figure 13:
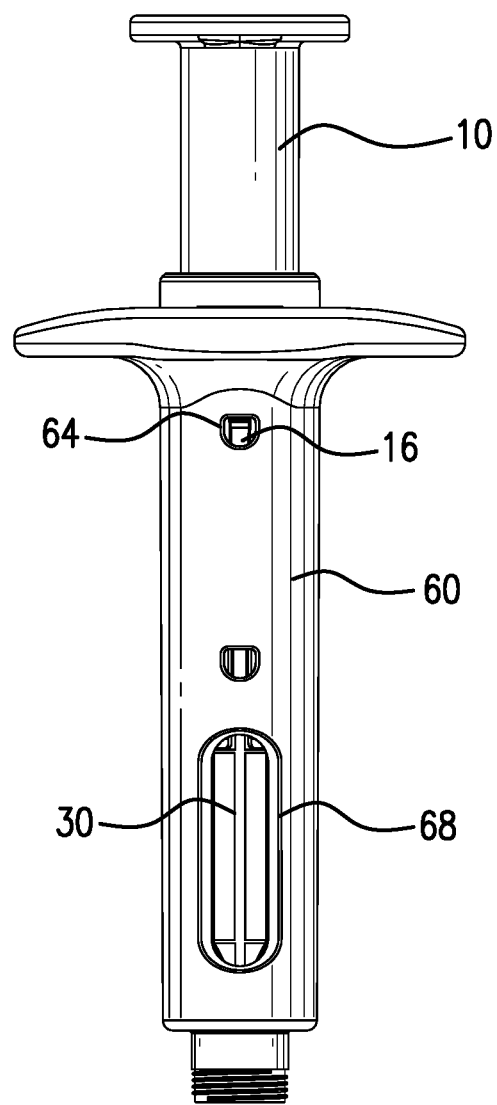
FIG. 13 is a perspective view of a plunger, drug container and body of an embodiment of the drug delivery device described herein.

FIG. 13 is a perspective view of one embodiment of the plunger, body and drug container of the drug delivery device described herein, wherein the plunger, body and drug container are assembled. As shown in FIG. 13, plunger 10 is telescopically engaged with body 60 and secured in an initial or first position by a pair of lift springs 16 (only one of the pair of lift springs are shown in FIG. 13) on the plunger 10 which are in communication with proximal notches 64 (only one of a pair of notches are shown in FIG. 13) on body 60. Also shown in FIG. 13 is window 68 located in the body to view the drug container 30.

Figure 14:
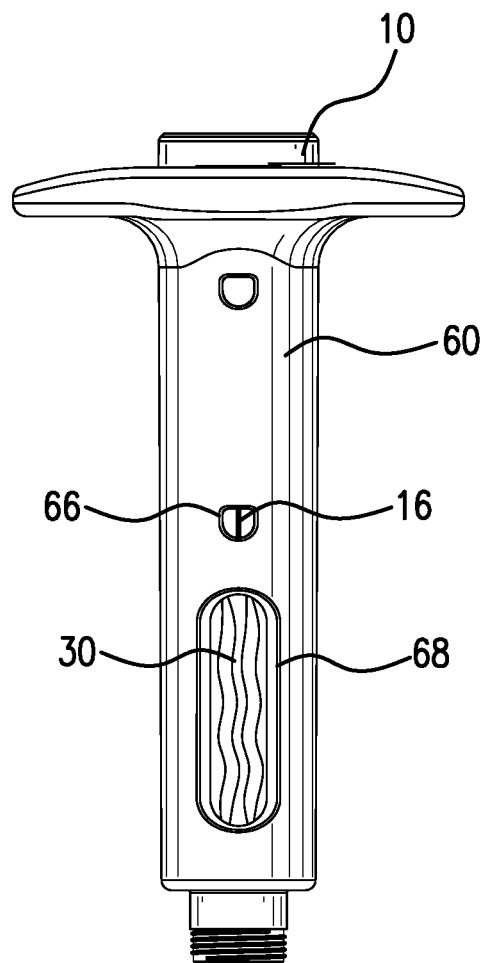
FIG. 14 is a perspective view of a plunger, drug container and body of an embodiment of the drug delivery device described herein.

FIG. 14 is a perspective view of one embodiment of the plunger, body and drug container of the drug delivery device described herein, wherein the plunger, body and drug container are assembled. As shown in FIG. 14, plunger 10 is telescopically engaged with body 60 and secured in final or second position by a pair of lift springs 16 (only one of the pair of lift springs are shown in FIG. 14) on the plunger 10 which are in communication with distal notches 66 (only one of a pair of notches are shown in FIG. 14) on body 60. Also shown in FIG. 14 is window 68 located in the body to view the drug container 30.

Figure 15:
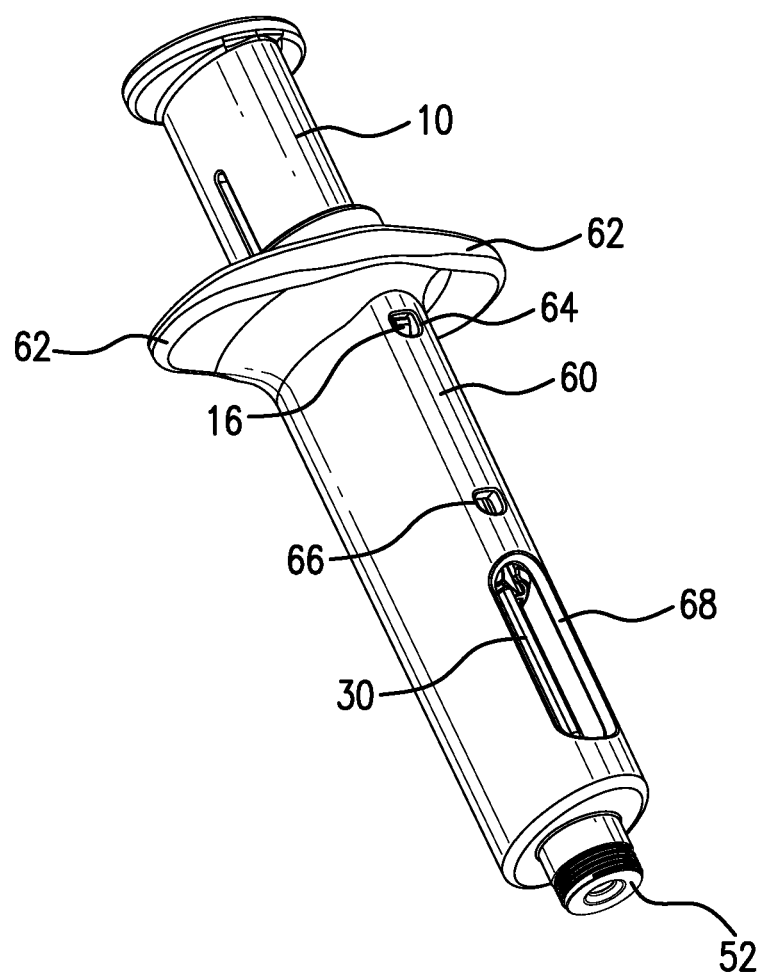
FIG. 15 is a perspective view of a plunger, drug container and body of an embodiment of the drug delivery device described herein.

FIG. 15 is a perspective view of one embodiment of the plunger, body and drug container of the drug delivery device described herein, wherein the plunger, body and drug container are assembled. As shown in FIG. 15, plunger 10 is telescopically engaged with body 60 and secured in an initial or first position by a pair of lift springs 16 (only one of the pair of lift springs are shown in FIG. 15) on the plunger 10 which are in communication with proximal notches 64 (only one of a pair of notches are shown in FIG. 15) on body 60. Also shown in FIG. 15 is window 68 located in the body 60 to view the drug container 30. Also shown in FIG. 15 are finger flanges 62 on the body 60. Also shown in FIG. 15 is an outlet port 52 which is capable of engaging with the outlet port on the drug container (not shown) and connecting a needle (not shown) with the body 60. In the embodiment shown in FIG. 15 the engagement between the body 60 and a needle is a threaded engagement.

Figure 16:
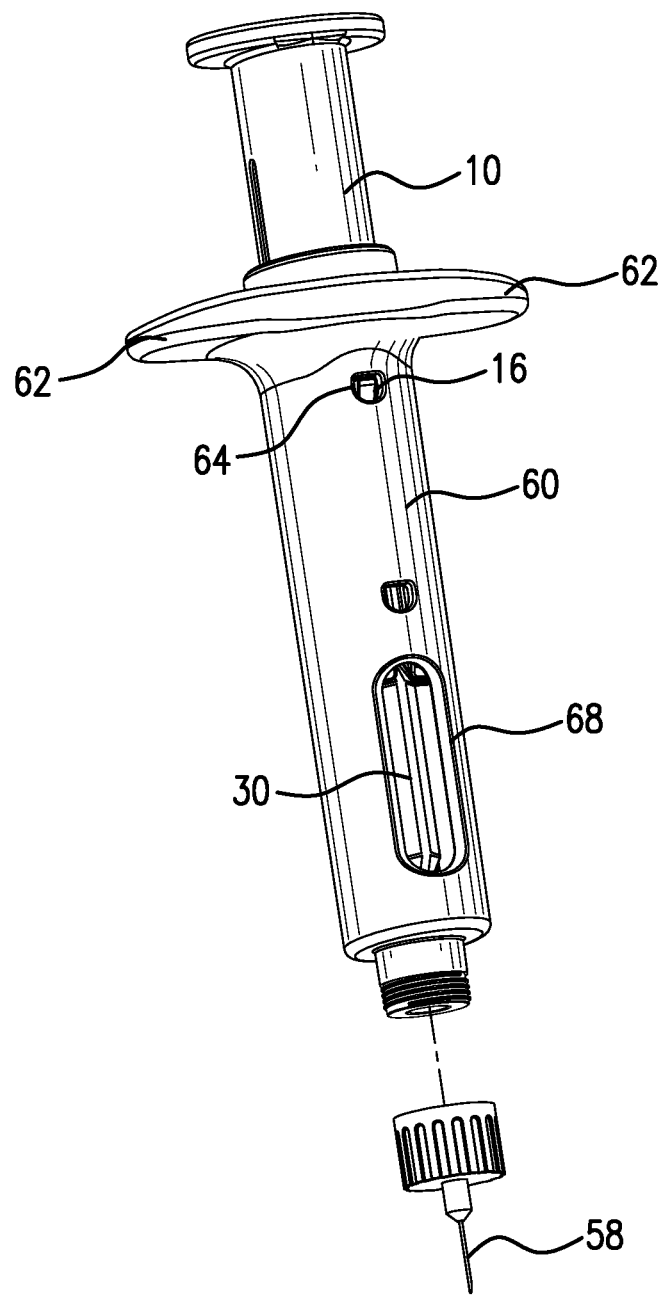
FIG. 16 is a perspective view of a plunger, drug container and body of an embodiment of the drug delivery device described herein.

FIG. 16 is a perspective view of one embodiment of the plunger, body and drug container of the drug delivery device described herein, wherein the plunger, body and drug container are assembled. As shown in FIG. 16, plunger 10 is telescopically engaged with body 60 and secured in an initial or first position by a pair of lift springs 16 (only one of the pair of lift springs are shown in FIG. 16) on the plunger 10 which are in communication with proximal notches 64 (only one of a pair of notches are shown in FIG. 16) on body 60. Also shown in FIG. 16 is window 68 located in the body to view the drug container 30, as well as finger flanges 62. Also shown in FIG. 16 is outlet port 52 which is capable of engaging with an outlet port on the drug container (not shown) and connecting a needle 58 with the body 60. In the embodiment shown in FIG. 16 the engagement between the body 60 and the needle 58 is a threaded engagement.

Figure 17:
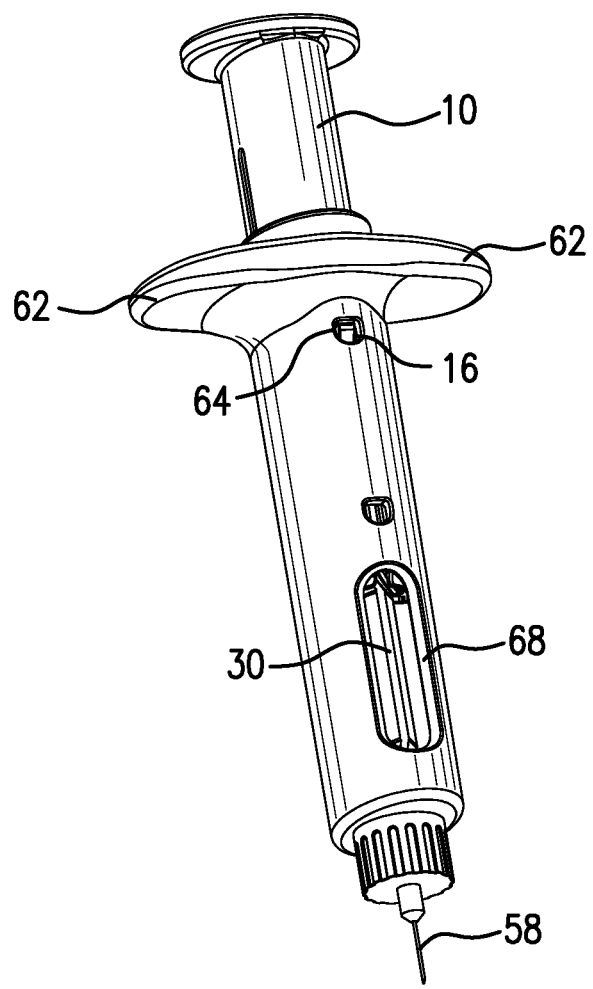
FIG. 17 is a perspective view of a plunger, drug container and body of an embodiment of the drug delivery device described herein.

FIG. 17 is a perspective view of one embodiment of the plunger, body and drug container of the drug delivery device described herein, wherein the plunger, body and drug container are assembled. As shown in FIG. 17, plunger 10 is telescopically engaged with body 60 and secured in an initial or first position by a pair of lift springs 16 (only one of the pair of lift springs are shown in FIG. 17) on the plunger 10 which are in communication with proximal notches 64 (only one of a pair of notches are shown in FIG. 17) on body 60. Also shown in FIG. 17 is window 68 located in the body to view the drug container 30. Also located on body 60 are finger flanges 62. Also shown in FIG. 17 is outlet port (not shown) that is connected a needle 58.

The drug delivery device can be used to deliver any type of drug product that can be delivered via a syringe. In some embodiments of the drug delivery device described herein, the drug container contains oxytocin or carbetocin. In certain embodiments of the drug delivery device described herein, the drug container is pre-filled with a drug or a formulation containing a drug. Suitable drugs include, but are not limited to, oxytocin or carbetocin.

Also described herein are methods of manufacturing the drug delivery devices described herein. In certain embodiments, the drug container is manufactured by blow-fill-seal technology (BFS).

The drug container and housing of the delivery devices described herein are preferably made of a biocompatible, non-biodegradable polymer. Suitable biocompatible, non-biodegradable polymers include but are not limited to, a polyacrylate; a polymer of ethylene-vinyl acetate; an acyl-substituted cellulose acetate; a non-degradable polyurethane; a polystyrene; a polyvinyl chloride; a polyvinyl fluoride; a poly(vinyl imidazole); a chlorosulphonate polyolefin; a polyethylene oxide; or a blend, combination, or copolymer thereof. Each component of the drug delivery device described herein can be made of the same or different biocompatible, non-biodegradable polymer.

The embodiments illustrated and discussed in this specification are intended only to teach those skilled in the art the best way known to the inventors to make and use the invention. Nothing in this specification should be considered as limiting the scope of the present invention. All drawings presented are representative and non-limiting. The above-described embodiments of the invention may be modified or varied, without departing from the invention, as appreciated by those skilled in the art in light of the above teachings. It is therefore to be understood that, within the scope of the claims and their equivalents, the invention may be practiced otherwise than as specifically described.

What is claimed is:

1. A drug delivery device comprising:
   a drug container extending between a distal end and a proximal end comprising an outlet port located at the distal end and wherein the drug container is capable of being compressed into a single plane;
   a body extending between a proximal end and a distal end of the body comprising a hollow space for containing the drug container; and
   a plunger extending between proximal end and a distal end of the plunger, wherein the distal end of the plunger engages telescopically with the proximal end of the body, wherein the plunger comprises at least one pair of cross-facing protrusions, wherein the at least one pair of cross-facing protrusions protrude toward and contact the drug container such that the drug container is compressed between the at least one pair of cross-facing protrusions as the plunger moves toward the distal end of the body.

2. The drug delivery device of claim 1, wherein the drug container contains a drug.

3. The drug delivery device of claim 1, wherein the drug container comprises a tapered distal portion located at the distal end of the drug container; a tapered proximal portion located at the proximal end of the drug container; and a central portion having a constant cross section located between the distal portion and the proximal portion of the drug container.

4. The drug delivery device of claim 3, wherein the central portion of the drug container has a hexagonal prism shape.

5. The drug delivery device of claim 1, wherein the at least one pair of cross-facing protrusions are at least two pairs of cross-facing protrusions.

6. The drug delivery device of claim 1, wherein the body comprises at least one finger flange located at the proximal end of the body.

7. The drug delivery device of claim 1, wherein the body comprises a pair of finger flanges located at the proximal end of the body.

8. The drug delivery device of claim 1, wherein the body comprises an outlet port that is capable of fitting telescopically over the outlet port of the drug container.

9. The drug delivery device of claim 8, further comprising a needle that attaches to the outlet port of the body and is in communication with the outlet port of the drug container.

10. The drug delivery device of claim 1, wherein the body comprises at least one pair of notches located proximal to the proximal end of the body.

11. The drug delivery device of claim 1, wherein the body comprises a pair of notches located proximal to the distal end of the body.

12. The drug delivery device of claim 11, wherein the plunger comprises one pair of lift springs that engage the pair of notches on the body to secure the drug delivery device in a locked position.

13. The drug delivery device of claim 1, wherein the body comprises at least one internal guide rail.

14. The drug delivery device of claim 13, wherein the plunger comprises a slot to engage the guide rail of the body.

15. A method of manufacturing the drug delivery device of claim 1 wherein, the drug container is made using blow-fill-seal technology.

* * * * *